United States Patent
de Wet et al.

(10) Patent No.: US 7,465,846 B2
(45) Date of Patent: Dec. 16, 2008

(54) EXTRACTION OF OXYGENATES FROM A HYDROCARBON STREAM

(75) Inventors: Johan Pieter de Wet, Vanderbijlpark (ZA); Wilhelmina Jansen, Vanderbijlpark (ZA); Paul Jacobson, Sasolburg (ZA)

(73) Assignee: Sasol Technology (Proprietary) Limited, Rosebank (ZA)

( * ) Notice: Subject to any disclaimer, the term of this patent is extended or adjusted under 35 U.S.C. 154(b) by 291 days.

(21) Appl. No.: 10/549,766

(22) PCT Filed: Mar. 10, 2004

(86) PCT No.: PCT/IB2004/000654

§ 371 (c)(1),
(2), (4) Date: May 8, 2006

(87) PCT Pub. No.: WO2004/080927

PCT Pub. Date: Sep. 23, 2004

(65) Prior Publication Data

US 2006/0258894 A1 Nov. 16, 2006

(30) Foreign Application Priority Data

Mar. 10, 2003 (ZA) ............................. 2003/1937
Aug. 21, 2003 (ZA) ............................. 2003/6523

(51) Int. Cl.
C07C 7/10 (2006.01)

(52) U.S. Cl. ............... 585/864; 585/867; 585/833; 585/834

(58) Field of Classification Search .............. None
See application file for complete search history.

(56) References Cited

U.S. PATENT DOCUMENTS

| 3,674,885 | A | 7/1972 | Griesinger et al. |
| 4,219,686 | A | 8/1980 | Petrillo et al. |
| 4,447,664 | A | 5/1984 | Murchison et al. |
| 4,513,156 | A | 4/1985 | Tabak |
| 4,603,225 | A | 7/1986 | Colaianne et al. |
| 4,686,317 | A | 8/1987 | Quann et al. |
| 5,196,624 | A | 3/1993 | Threlkel et al. |

(Continued)

FOREIGN PATENT DOCUMENTS

DE 199 11 910 A1 9/2000

(Continued)

OTHER PUBLICATIONS

Kocal et al., "Production of linear alkylbanzene," *Catalysis*, 2001 (CAS Abstract No. 136:249302).

(Continued)

*Primary Examiner*—Tam M Nguyen
(74) *Attorney, Agent, or Firm*—Brinks Hofer Gilson & Lione

(57) ABSTRACT

This invention relates to a commercially viable process for extracting oxygenates from a hydrocarbon stream, typically a fraction of the condensation product of a Fischer-Tropsch reaction, while preserving the olefin content of the condensation product. The oxygenate extraction process is a liquid-liquid extraction process that takes place in an extraction column using a polar organic solvent, such as methanol, and water as the solvent, wherein the polar organic solvent and water are added separately to the extraction column.

18 Claims, 2 Drawing Sheets

U.S. PATENT DOCUMENTS

| | | |
|---|---|---|
| 5,196,625 A | 3/1993 | Threlkel et al. |
| 6,111,158 A | 8/2000 | Marinangeli et al. |
| 6,375,830 B1 | 4/2002 | Clark et al. |
| 6,392,109 B1 | 5/2002 | O'Rear et al. |
| 2002/0082182 A1 | 6/2002 | Kott et al. |
| 2002/0115732 A1 | 8/2002 | Moore, Jr. et al. |

FOREIGN PATENT DOCUMENTS

| | | |
|---|---|---|
| EP | 0 807 616 A2 | 11/1997 |
| EP | 1 160 309 A1 | 12/2001 |
| GB | 669313 | 4/1952 |
| GB | 990744 | 4/1965 |
| GB | 2 258 258 A | 2/1993 |
| WO | WO 90/11986 A1 | 10/1990 |
| WO | WO 99/05082 A1 | 2/1999 |
| WO | WO 99/05241 A1 | 2/1999 |
| WO | WO 99/05242 A1 | 2/1999 |
| WO | WO 00/14184 A2 | 3/2000 |
| WO | WO 01/02325 A1 | 1/2001 |
| WO | WO 01/64610 A1 | 9/2001 |
| WO | WO 02/31085 A2 | 4/2002 |
| WO | WO 02/44114 A1 | 6/2002 |

OTHER PUBLICATIONS

Marr et al., "Recent Innovations in linear alkylbenzene process technology," *World Surfactants Congress*, May 29-Jun. 2, 2000, (CAS Abstract No. 136:249396).

Sharma et al., "Synthesis of detergents from Fischer-Tropsch waxes: Part I. Synthesis of heptyl benzene sulphonate," *Research and Industry*, Sep. 20, 1975.

Sharma et al., "Synthesis of detergents from Fischer-Tropsch waxes: Part II. Synthesis of docedyl benzene sulphonate," *Indian J. Technology*, 1977 (CAS Abstract No. 89:56861).

EXTRACTION OF OXYGENATES FROM A HYDROCARBON STREAM

BACKGROUND OF THE INVENTION

This invention relates to a process for extracting oxygenates from a hydrocarbon stream.

Many processes for extracting oxygenates from hydrocarbon streams are known. Such extraction methods include hydrogenation, azeotropic distillation, extractive distillation, vapour phase dehydration, liquid phase dehydration and liquid-liquid extraction.

United Kingdom Patent No. 669,313 in the name of California Research Corporation discloses the use of a hydrocarbon condensate from the Fischer-Tropsch process as a feedstock in the production of alkyl benzene. This reference is limited to the use of "high temperature" Fischer-Tropsch processes wherein the Fischer-Tropsch reaction is carried out temperatures of approximately 300° C. and higher, for the production of the hydrocarbon condensate. This reference states that Fischer Tropsch feedstock produced results in poor quality Linear Alkyl Benezene due to odour and wetting problems caused by carbonyl i.e. oxygenate content of the Fischer Tropsch feedstock. Methods suggested for removing the oxygenates include treating the stocks with hot caustic solution or sodium bisulphite followed by extraction with solvents such as methanol, or treatment with boric acid solution to form esters which can be removed by distillation. The preferred method for addressing this problem is by adsorption of carbonyl compounds from the Fischer Tropsch feedstock using activated carbon and silica gel. This process is only feasible for feeds with low oxygenate concentrations. Also, in the example the olefin recovery is less than 25%, i.e. the olefin content is not preserved.

United Kingdom Patent No. 661,916 in the name of Naamlooze Vennootschap De Batafsche Petroleum Maatschappij relates to a method of separating oxygenated compounds from the reaction product of a Fischer-Tropsch reaction by extraction using liquid sulphur dioxide and a paraffinic hydrocarbon flowing in countercurrent to each other. This reference provides that the separation of the oxygenated compounds by extraction with a single solvent, such as liquid sulphur dioxide or aqueous methanol has proved difficult and uneconomic in practice.

This invention relates to a commercially viable process for extracting or separating oxygenates from a hydrocarbon stream containing olefins and paraffins, typically the condensation product of a Fischer-Tropsch reaction, while preserving the olefin content of the stream.

SUMMARY OF THE INVENTION

According to the invention there is provided a commercially viable process for extracting oxygenates from a hydrocarbon stream, typically a fraction of the condensation product of a Fischer-Tropsch reaction, while preserving the olefin content of the condensation product.

The oxygenate extraction process is a liquid-liquid extraction process that preferably takes place in an extraction column using a polar organic solvent, preferably methanol, and water as the solvent, wherein the polar organic solvent and water are added separately to the extraction column.

The hydrocarbon stream is fed into the extraction column at, or near, the bottom thereof, a polar organic solvent stream is fed into the extraction column at, or near, the top thereof, and a water stream is fed into the extraction column between the hydrocarbon stream and polar organic solvent stream.

An extract from the liquid-liquid extraction may be sent to a solvent recovery column from which a tops product comprising polar organic solvent, olefins and paraffins is recycled to the extraction column, thereby enhancing the overall recovery of olefins and paraffins. A bottoms product from solvent recovery column may also be recycled to the extraction column.

A raffinate stream from the extraction column is preferably sent to a stripper column from which a hydrocarbon stream containing more than 90% by weight olefins and paraffins and typically less than 0.2% by weight, preferably less than 0.02% by weight, most preferably less than 0.01% by weight oxygenates exits as a bottoms product. The recovery of olefins and paraffins over the oxygenate extraction process is preferably greater than 70%, more preferably greater than 80%, while the olefin/paraffin ratio is at least substantially preserved.

The solvent preferably has a water content of more than 3% by weight, more preferably a water content of about 5%-15% by weight.

The hydrocarbon stream may be the condensation product of a low temperature Fischer-Tropsch reaction carried out at a temperature of 160° C.-280° C., preferably 210° C.-260° C., and a Fischer-Tropsch catalyst, preferably in the presence of a cobalt catalyst to provide a hydrocarbon condensate containing 60 to 80% by weight paraffins and 10 to 30% by weight, typically less than 25% by weight, olefins. The olefins so produced have a high degree of linearity of greater than 92%, typically greater than 95%. The paraffins so produced have a degree of linearity of greater than 92%.

The hydrocarbon condensate product is typically fractionated into the $C_8$ to $C_{16}$ detergent range, preferably into the $C_{10}$ to $C_{13}$ range prior to extraction. Typically, the hydrocarbon stream is a fractionated hydrocarbon condensate product from a low temperature Fischer-Tropsch reaction in the $C_{10}$ to $C_{13}$ range containing 10 to 30%, typically less than 25%, by weight olefins with a high degree of linearity of greater than 92%, typically greater than 95%, 60% to 80% by weight paraffins and 5% to 15% by weight oxygenates.

DESCRIPTION OF PREFERRED EMBODIMENTS

Figure 1:
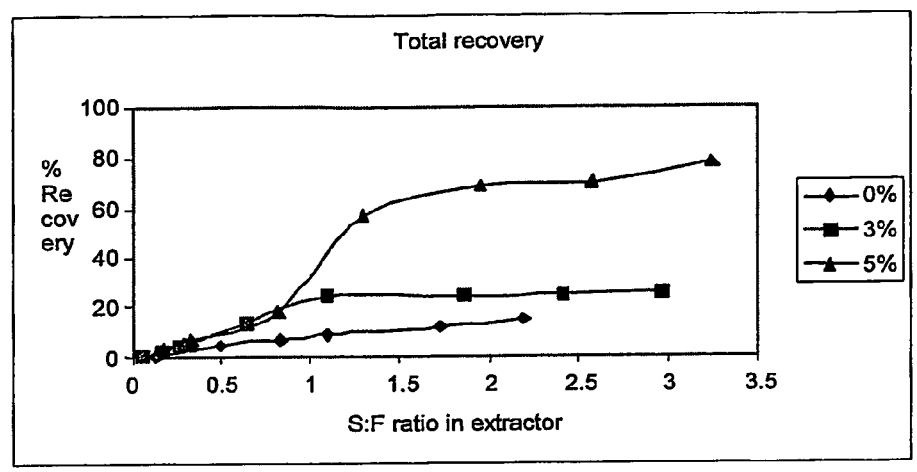
FIG. 1 is a graph showing the percent recovery of olefins and paraffins in a solvent recovery column at different solvent to feed ratios for solvents containing methanol and 0, 3 and 5% water.

This invention relates to a process for extracting oxygenates from a hydrocarbon condensate stream from a Fischer-Tropsch reaction. The substantially oxygenate-free hydrocarbon stream can be used in the production of linear alkyl benzene.

In the Fischer-Tropsch process, synthesis gas (carbon monoxide and hydrogen) obtained either from the gasification of coal or the reforming of natural gas, is reacted over a Fischer Tropsch catalyst to produce a mixture of hydrocarbons ranging from methane to waxes and smaller amounts of oxygenates.

In a low temperature Fischer-Tropsch reaction, the reaction takes place in a slurry bed reactor or fixed bed reactor, preferably a slurry bed reactor, at a temperature in the range of 160° C.-280° C., preferably 210° C.-260° C., and a pressure in the range of 18-50 bar (gauge), preferably between 20-30 bar (gauge), in the presence of a catalyst. The catalyst may include iron, cobalt, nickel or ruthenium. However, a cobalt-based catalyst is preferred for the low temperature reaction. Usually, the cobalt catalyst is supported on an alumina support.

During the low temperature Fischer-Tropsch reaction, a lighter hydrocarbon vapour phase is separated from a liquid phase comprising heavier liquid hydrocarbon products. The heavier liquid hydrocarbon product (waxy products) is the major product of the reaction and may, for example, be hydro-cracked to produce diesel and naphtha.

The lighter hydrocarbon vapour phase which comprises gaseous hydrocarbon products, unreacted synthesis gas and water is condensed to provide a "condensation product" which comprises an aqueous phase and a hydrocarbon condensation product phase.

The hydrocarbon condensation product includes olefins, paraffins in the $C_4$ to $C_{26}$ range, and oxygenates including alcohols, esters, aldehydes, ketones and acids.

Typically, a hydrocarbon condensation product for a low temperature Fischer-Tropsch reaction contains 10%-30% by weight olefins, 60%-80% by weight paraffins, and 5%-10% by weight oxygenates. It has, surprisingly, been found that even though this condensation product contains oxygenates and has a low olefin content, it can be used in the production of linear alkyl benzene. However, it is necessary to first extract the oxygenates as these species have a negative effect on the alkylation reaction. There is therefore a need to find a process for extracting oxygenates, but at the same time preserve the olefin concentent. For the production of linear alkyl benzene, the hydrocarbon condensate product is fractionated into a $C_{10}$-$C_{13}$ cut which, by way of example, contains 25% by weight olefins, 68% by weight paraffins and 7% by weight oxygenates. The oxygenate content of this $C_{10}$-$C_{13}$ cut can be as high as 15%.

In the prior art, many methods of extracting oxygenates from hydrocarbon streams are suggested. Such removal methods include hydrogenation, azeotropic distillation, extractive distillation, vapour phase dehydration, liquid phase dehydration and liquid-liquid extraction. It has been found that liquid-liquid extraction is a preferred method of oxygenate extraction because, if the correct solvent is selected, the olefin concentent can be preserved. In liquid-liquid extraction, the solvent can be any polar material that has partial miscibility with the feed stream 14, such as tri-ethanol amine, tri-ethylene glycol with between zero and 20% water, acetonitrile with between 5% and 20% water, acetol, diols, methanol, or ethanol and water.

According to the invention, a preferred solvent in a liquid-liquid extraction column is a polar organic solvent and water. To be useful in this invention, the polar organic solvent needs to be low-boiling and either preferably non-azeotroping with water, or form an azeotrope with water that has low water content. A suitable polar organic solvent is methanol. Usually, this type of solvent would be added as a mixture at the top of the liquid-liquid extraction column. It has been found that it is possible to obtain a higher recovery of olefins and paraffins, with a lower oxygenate content (i.e. a purer product) by adding the polar organic solvent and the water separately to the liquid-liquid extraction column.

Another aspect of the invention is that, normally, a high-boiling point solvent is preferred because the solvent recovery steps after extraction require less energy than will be the case for a low-boiling point solvent. However, it has been found that a mixture of methanol and water, which is a low-boiling point solvent, need not suffer from this drawback, because it can be effective at low solvent to feed ratios (this can be lower than 1 if the required oxygenate extraction is not too severe). Furthermore, one would not expect to be able to use methanol and water as a solvent in a liquid-liquid extraction column to extract oxygenates from the abovementioned hydrocarbon condensate because a study of the different azeotropes with water that exist in the hydrocarbon condensate would lead one to expect that it would not be possible to distil water in a solvent recovery column without azeotroping oxygenates overhead as well. Surprisingly, this turns out not to be the case.

Figure 2:
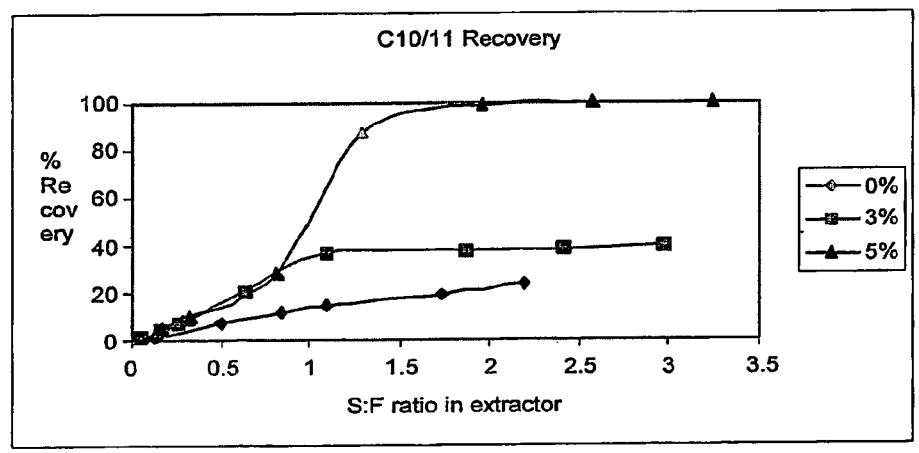
FIG. 2 is a graph showing the C10/11 olefin and paraffin recovery in a solvent recovery column at different solvent to feed ratios for solvents containing methanol and 0, 3 and 5% water.

Thus, a further aspect of the invention is that is has been found that a water/methanol solvent, preferably with greater than 3% by weight water content in the liquid-liquid extraction column leads to better recovery of desired products in the solvent recovery column than a dry methanol solvent or a water/methanol solvent with less than 3% by weight water in the liquid-liquid extraction column. This is shown in FIG. 1, from which it can be seen that a methanol/water solvent with 5% by weight water provides as much as 80% recovery of olefins and paraffins in the solvent recovery column. FIG. 2 shows that almost a 100% recovery of C10/C11 olefins and paraffins in the solvent recovery column is possible.

Thus, according to the invention, typically 90% of the olefins and paraffins are recovered from the liquid-liquid extraction column. The 10% of olefins and paraffins not recovered are sent to the solvent recovery column in the extract from the liquid-liquid extraction column. Up to 60% of the olefins and paraffins in the solvent recovery column are recovered in the overheads product from the solvent recovery column and recycled to the liquid-liquid extraction column. This results in an over-all recovery of olefins and paraffins of more than 90%. The olefin/paraffin ratio is also substantially preserved.

Figure 3:
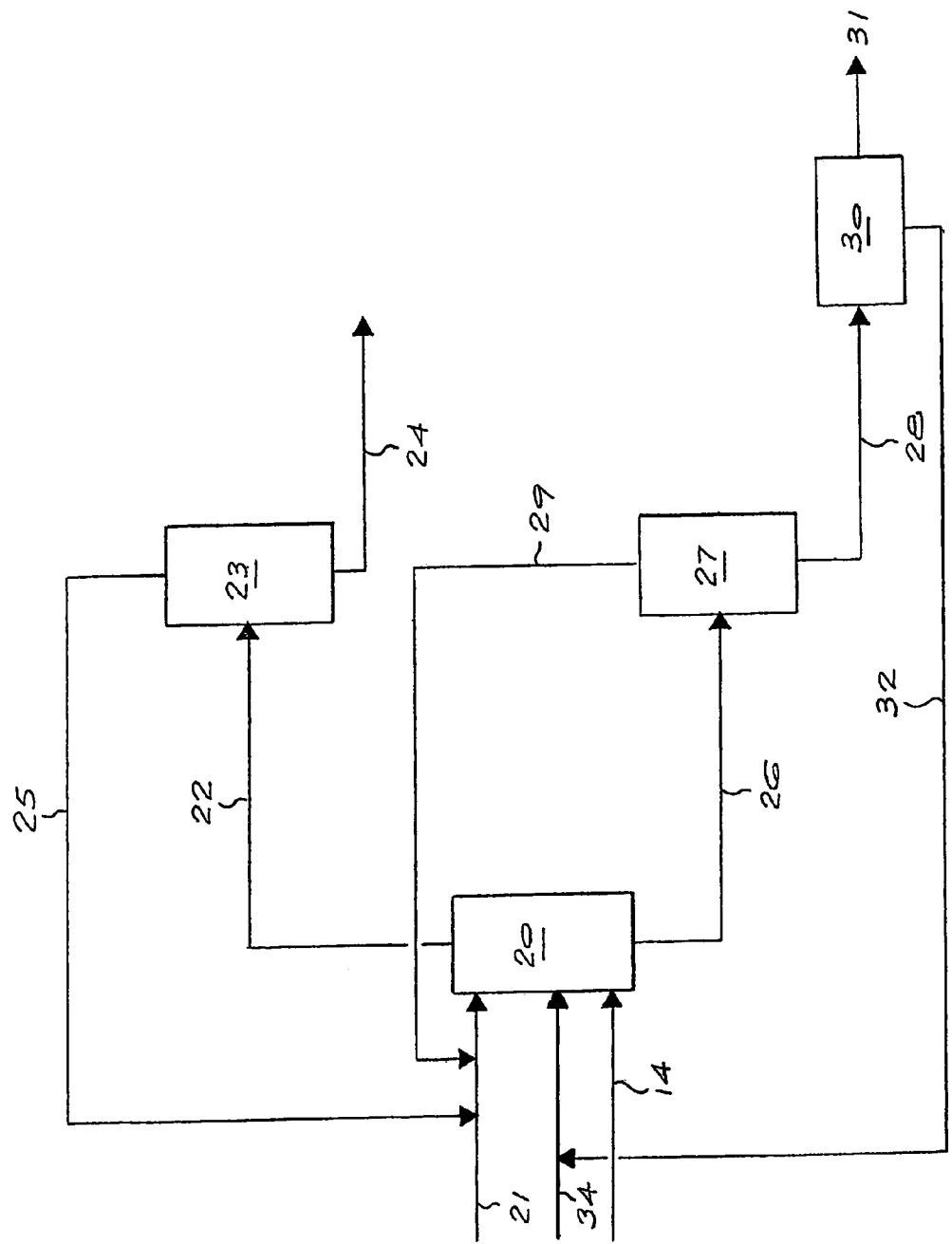
FIG. 3 is a block diagram of a process of the invention for extracting oxygenates from a hydrocarbon stream.

With reference FIG. 3, a liquid-liquid extraction process of the invention includes a liquid-liquid extraction column 20. The fractionated condensation product of a low temperature Fischer-Tropsch reaction described above 14 is fed into the extraction column 20 at, or near, the bottom thereof. The solvent for the extraction column 20 is water and methanol. According to the invention, the water and methanol are added to the extraction column 20 separately. Methanol is added to the extraction column 20 via a methanol stream 21 at, or near, the top of the extraction column 20. Water is added to the extraction column 20 via a water stream 34 located between the hydrocarbon stream 14 and methanol stream 21. The flow of methanol and water is controlled to provide a solvent in the column with more than 5% by weight water. The solvent to feed ratio in the extraction column 20 is low, typically less than 1.5.

Raffinate 22 from the top of the extraction column 20, which includes olefins and paraffins and a small amount of solvent, enters a raffinate stripper column 23 and a hydrocarbon product stream comprising more than 90% by weight olefins and paraffins and less than 0.01% by weight oxygenates exits as a bottoms product 24. The bottoms product 24, which shows an overall recovery of over 90% of the olefins and paraffins, contains more than 20% by weight α-olefins and more than 70% by weight n-paraffins. Thus, the olefin content of the hydrocarbon product (which is intended for use in the production of linear alkyl benzene) has been preserved. A solvent comprising mainly methanol (more than 90% by weight) and low concentrations of water (less than 5% by weight) and olefins/paraffins (less than 5% by weight) exits as a tops product 25 and is returned to the solvent feed stream 21. If it is desired to recover the bottoms product 24 as a vapour stream, this can be done by taking a bottoms vapour stream from the column 20. The liquid product from the column 20 will then be a very small effluent stream.

An extract 26 is drawn from the bottom of the extraction column 20 and is fed to a solvent recovery column 27. A tops product 29 from the solvent recovery column 27 comprises over 90% by weight methanol and 2% by weight olefins and paraffins. Up to 60% of the olefins and paraffins from the extract 26 are recovered to the tops product 29. The tops product is then recycled to the solvent stream 21. The oxygenate content of the tops product 29 can be as low as 50 ppm, depending on the solvent to feed ratio used in the extraction column 20. A bottoms product 28 from the solvent recovery column 27 comprises mainly water, oxygenates and olefins/paraffins. This bottoms product 28 forms two liquid phases that can be decanted in a decanter 30. The organic phase is an oxygenate, olefin and paraffin stream 31, which leaves the process as a product. The aqueous phase is a stream 32, which is recycled to the extraction column 20 via the water stream 34.

The presence of water in the extraction column 20 improves the recovery of paraffins and olefins in the raffinate stream 22. Although it is important for the water to be present in the lower section of the extraction column 20, including the point where the extract 26 is drawn from the extraction column 20, it has been found that it is not necessary for the water to be present throughout the extraction column 20. It has also been found that it is beneficial to have as little water as possible at the top of the extraction column 20 as the presence of water lowers the methanol's ability to take up oxygenates which would result in a higher solvent to feed ratio when compared to dry methanol. Thus, if as little water as possible is present in the upper section of the extraction column 20 it is beneficial in that it is possible to use a lower solvent to feed ratio than when water is added as a mixture together with methanol. Adding the water separately into the extraction column 20 between the hydrocarbon stream 14 and methanol stream 21 results in an improved paraffin and olefin recovery with better raffinate 22 purity than if the water and methanol were added as a mixture. As mentioned above, the aqueous phase stream 32 recovered from the decanter 30 is recycled to the water stream 34 into the extractor column 20. The stream 32 may contain oxygenates and the addition of this water at a different point to the methanol stream 21 lower down the extraction column 20 ensures that oxygenates are cleaned from the stream in-the column, before they can appear in the raffinate stream 22.

This invention has the added benefit that the solvent recovery column 27 and decanter 30 results in a water-enriched solvent stream 32 that can be fed lower down the extraction column 20. The solvent recovery column 27 overheads and raffinate column 23 overheads forms a suitable methanol-enriched solvent stream 21 that can be fed to near the top of the extraction column 20. This is advantageous, since no additional work-up of the solvent is required to produce methanol- and water-enriched solvent streams.

When operating a solvent recovery column 27 in the manner described above, it is to be expected that certain species may become trapped in the column. These species, will tend to build up and in the process cause unstable operation of the solvent recovery column. Such species would typically be heavier olefins and paraffins or lighter oxygenates in the present case. Operating the solvent recovery column with a small side draw may prevent the build up of such species and thereby result in much improved operability of the system.

After passing the $C_{10}$-$C_{13}$ hydrocarbon feed stream mentioned above through the abovementioned oxygenate extraction process using a mixture of methanol (95% by weight) and water (5% by weight) and a solvent to feed ratio of 1.25, the purified hydrocarbon feed stream contains 22% by weight olefins, 76% by weight paraffins and less than 0.02% by weight oxygenates. Not only does the extraction process extract oxygenates, it also preserves the olefin content of the hydrocarbon feed. The purified hydrocarbon feed stream containing olefins is particularly useful in the production of linear alkyl benzene.

With reference to Comparative Example 1 and Examples 2 and 3 of the invention below, it is evident that the process of the invention where the water and methanol are added separately leads to a lower oxygenate content in the product stream 24. Example 2 provides an oxygenate content of 0.0094% by weight in the product stream 24, while comparative Example 1 provides an oxygenate content of 0.0145% by weight in the product stream 24. Thus the product of Example 2 of the invention provides a more suitable hydrocarbon feed stream for use in the production of linear alkyl benzene, than the product of comparative Example 1. Example 2 of the invention also shows a higher overall olefin and paraffin recovery than comparative Example 1. Example 3 of the invention is of an oxygenate removal process for a feed stream 14 which has a relatively high oxygenate content, of approximately 13% by weight.

The invention will now be described in more detail with reference to the following non-limiting Examples 2 and 3 and comparative Example 1.

COMPARATIVE EXAMPLE 1

This example shows a comparative process where the water and methanol are introduced to the extraction column together in the solvent feed stream 21, and the stream 32 is recycled to the solvent feed stream 21. The extraction column 20 was run at a solvent to feed ratio of 1.25 and a temperature of 50° C. The overall olefin/paraffin recovery in the stream 24 was 89.9% with a remaining oxygenate content of 0.0145%. The olefin/paraffin ratio in the feed was 1:3.7 and 1:3.6 post oxygenate extraction. The olefin/paraffin ratio was therefore substantially preserved.

Extraction column 20

|  | 14 | | 21 | | 22 | | 26 | |
| --- | --- | --- | --- | --- | --- | --- | --- | --- |
| Stream | Comp (wt %) | Flow (kg/hr) | Comp (wt %) | Flow (kg/hr) | Comp (wt %) | Flow (kg/hr) | Comp (wt %) | Flow (kg/hr) |
| Total | 100 | 3000 | 100 | 3750 | 100 | 2530 | 100 | 4220 |
| Total C10-C13 P/O | 92.7 | 2779.7 | 2.16 | 81.0 | 99.1 | 2507.9 | 6.20 | 261.7 |
| Total Oxygenates | 7.3 | 217.7 | 0.000 | 0.000 | 0.0144 | 0.365 | 5.78 | 243.7 |
| Lights and Heavies | 0.057 | 1.7 | 0.004 | 0.144 | 0.0104 | 0.263 | 0.00480 | 0.202 |

-continued

| | 14 | | 21 | | 22 | | 26 | |
|---|---|---|---|---|---|---|---|---|
| Stream | Comp (wt %) | Flow (kg/hr) | Comp (wt %) | Flow (kg/hr) | Comp (wt %) | Flow (kg/hr) | Comp (wt %) | Flow (kg/hr) |
| Water | 0.031 | 0.934 | 6.01 | 225.6 | 0.0073 | 0.184 | 5.74 | 242.4 |
| Methanol | 0.000 | 0.000 | 91.7 | 3443.3 | 0.842 | 21.31 | 82.3 | 3472.0 |

Raffinate Stripper column 23

| | 22 | | 25 | | 24 | |
|---|---|---|---|---|---|---|
| Stream | Comp (wt %) | Flow (kg/hr) | Comp (wt %) | Flow (kg/hr) | Comp (wt %) | Flow (kg/hr) |
| Total | 100 | 2530 | 100 | 30 | 100 | 2500 |
| Total C10-C13 P/O | 99.1 | 2507.9 | 2.63 | 0.793 | 99.97 | 2499.4 |
| Total Oxygenates | 0.0144 | 0.365 | 0.00163 | 0.000491 | 0.0145 | 0.363 |
| Lights and Heavies | 0.0104 | 0.263 | 0.0887 | 0.0267 | 0.00808 | 0.202 |
| Water | 0.0073 | 0.184 | 1.52 | 0.456 | 0.00115 | 0.0288 |
| Methanol | 0.842 | 21.31 | 95.4 | 28.7 | 0.000 | 0.000 |

Solvent Recovery column 27

| | 26 | | 29 | | 28 | |
|---|---|---|---|---|---|---|
| Stream | Comp (wt %) | Flow (kg/hr) | Comp (wt %) | Flow (kg/hr) | Comp (wt %) | Flow (kg/hr) |
| Total | 100 | 4220 | 100 | 3584 | 100 | 636 |
| Total C10-C13 P/O | 6.20 | 261.7 | 2.37 | 85.1 | 27.6 | 175.8 |
| Total Oxygenates | 5.78 | 243.7 | 0.00140 | 0.0503 | 42.0 | 267.0 |
| Lights and Heavies | 0.00480 | 0.202 | 0.00747 | 0.268 | 0.00279 | 0.0177 |
| Water | 5.74 | 242.4 | 1.30 | 46.8 | 29.3 | 186.6 |
| Methanol | 82.3 | 3472.0 | 96.2 | 3451.9 | 1.04 | 6.63 |

EXAMPLE 2

This example shows a process according to the invention where the methanol and water are introduced to the extraction column in separate streams 21 and 34 respectively. The extraction column 20 was run at a solvent to feed ratio of 1.2 and a temperature of 50° C. The overall olefin/paraffin recovery in the stream 24 was 92.3% with a remaining oxygenate content of 0.0094%. The olefin/paraffin ratio in the feed was 1:3.7 and 1:3.6 post oxygenate extraction. The olefin/paraffin ratio was therefore substantially preserved.

Extraction column 20

| | 14 | | 34 | | 21 | | 22 | | 26 | |
|---|---|---|---|---|---|---|---|---|---|---|
| Stream | Comp (wt %) | Flow (kg/hr) | Comp (wt %) | Flow (kg/hr) | Comp (wt %) | Flow (kg/hr) | Comp (wt %) | Flow (kg/hr) | Comp (wt %) | Flow (kg/hr) |
| Total | 100 | 3000 | 100 | 179 | 100 | 3334 | 100 | 2599 | 100 | 3914 |
| Total C10-C13 P/O | 92.6 | 2778.8 | 0.000 | 0.000 | 2.11 | 70.3 | 99.0 | 2572.1 | 7.89 | 308.8 |
| Total Oxygenates | 7.34 | 220.3 | 0.000 | 0.000 | 0.000 | 0.000 | 0.00937 | 0.244 | 6.00 | 234.9 |
| Lights and Heavies | 0.0156 | 0.470 | 0.000 | 0.000 | 0.009 | 0.298 | 0.00292 | 0.0758 | 0.00813 | 0.318 |
| Water | 0.0164 | 0.492 | 94.9 | 169.9 | 0.29 | 9.7 | 0.00270 | 0.0702 | 4.89 | 191.4 |
| Methanol | 0.000 | 0.000 | 5.07 | 9.07 | 97.6 | 3253.7 | 1.02 | 26.5 | 81.2 | 3178.6 |

Raffinate Stripper column 23

| Stream | 22 Comp (wt %) | 22 Flow (kg/hr) | 25 Comp (wt %) | 25 Flow (kg/hr) | 24 Comp (wt %) | 24 Flow (kg/hr) |
|---|---|---|---|---|---|---|
| Total | 100 | 2599 | 100 | 33 | 100 | 2566 |
| Total C10-C13 P/O | 99.0 | 2572.1 | 2.01 | 0.663 | 99.98 | 2565.733 |
| Total Oxygenates | 0.00937 | 0.244 | 0.00647 | 0.00213 | 0.0094 | 0.24122 |
| Lights and Heavies | 0.00292 | 0.0758 | 0.0708 | 0.0234 | 0.000488 | 0.0125 |
| Water | 0.00270 | 0.0702 | 0.210 | 0.0693 | 0.000500 | 0.0128 |
| Methanol | 1.02 | 26.5 | 97.7 | 32.2 | 0.000 | 0.0 |

Solvent Recovery column 27

| Stream | 26 Comp (wt %) | 26 Flow (kg/hr) | 29 Comp (wt %) | 29 Flow (kg/hr) | 28 Comp (wt %) | 28 Flow (kg/hr) |
|---|---|---|---|---|---|---|
| Total | 100 | 3914 | 100 | 3171 | 100 | 743 |
| Total C10-C13 P/O | 7.89 | 308.8 | 2.01 | 63.8 | 34.8 | 258.4 |
| Total Oxygenates | 6.00 | 234.9 | 0.00335 | 0.1 | 32.9 | 244.8 |
| Lights and Heavies | 0.00813 | 0.318 | 0.00237 | 0.075 | 0.00869 | 0.0646 |
| Water | 4.89 | 191.4 | 0.22 | 7.0 | 28.7 | 213.6 |
| Methanol | 81.2 | 3178.6 | 97.8 | 3100.0 | 3.51 | 26.09 |

EXAMPLE 3

This example shows a process according to the invention where the methanol and water are introduced to the extraction column in separate streams 21 and 34 respectively. The extraction column 20 was run at a solvent to feed ratio of 2:1 and a temperature of 50° C. The overall olefin/paraffin recovery in the stream 24 was 91.4%. Once again the olefin/paraffin ratio was substantially preserved.

Extraction column 20

| Stream | 14 Comp (wt %) | 14 Flow (kg/hr) | 32 Comp (wt %) | 32 Flow (kg/hr) | 21 Comp (wt %) | 21 Flow (kg/hr) | 22 Comp (wt %) | 22 Flow (kg/hr) | 26 Comp (wt %) | 26 Flow (kg/hr) |
|---|---|---|---|---|---|---|---|---|---|---|
| Total | 100 | 3000 | 100 | 600 | 100 | 5400 | 100 | 2413 | 100 | 6587 |
| Total C10-C13 P/O | 86.9 | 2606.9 | 0.000 | 0.001 | 6.57 | 355.0 | 98.8 | 2383.2 | 8.79 | 578.7 |
| Total Oxygenates | 12.91 | 387.4 | 0.082 | 0.489 | 0.000 | 0.000 | 0.00848 | 0.205 | 5.89 | 387.7 |
| Lights and Heavies | 0.1913 | 5.739 | 0.000 | 0.000 | 0.000 | 0.013 | 0.20636 | 4.9799 | 0.01173 | 0.773 |
| Water | 0.0000 | 0.000 | 99.9 | 599.5 | 1.96 | 105.8 | 0.00316 | 0.0762 | 10.71 | 705.2 |
| Methanol | 0.000 | 0.000 | 0.01 | 0.04 | 91.5 | 4939.2 | 1.03 | 24.8 | 74.6 | 4914.5 |

Raffinate Stripper column 23

| Stream | 22 Comp (wt %) | 22 Flow (kg/hr) | 25 Comp (wt %) | 25 Flow (kg/hr) | 24 Comp (wt %) | 24 Flow (kg/hr) |
| --- | --- | --- | --- | --- | --- | --- |
| Total | 100 | 2413 | 100 | 26 | 100 | 2387 |
| Total C10-C13 P/O | 98.8 | 2383.2 | 3.92 | 1.012 | 99.78 | 2382.148 |
| Total Oxygenates | 0.00848 | 0.205 | 0.00063 | 0.00016 | 0.0086 | 0.20468 |
| Lights and Heavies | 0.206 | 4.9799 | 0.0006 | 0.0002 | 0.209 | 4.9797 |
| Water | 0.00316 | 0.0762 | 0.294 | 0.0761 | 0.000007 | 0.0002 |
| Methanol | 1.03 | 24.8 | 95.8 | 24.7 | 0.001 | 0.0 |

Solvent Recovery column 27

| Stream | 26 Comp (wt %) | 26 Flow (kg/hr) | 25 Comp (wt %) | 25 Flow (kg/hr) | 29 Comp (wt %) | 29 Flow (kg/hr) | 28 Comp (wt %) | 28 Flow (kg/hr) |
| --- | --- | --- | --- | --- | --- | --- | --- | --- |
| Total | 100 | 6587 | 100 | 26 | 100 | 5400 | 100 | 1213 |
| Total C10-C13 P/O | 8.79 | 578.7 | 3.92 | 1.012 | 6.57 | 355.0 | 18.5 | 224.7 |
| Total Oxygenates | 5.89 | 387.7 | 0.00063 | 0.00016 | 0.00000 | 0.0 | 32.0 | 387.7 |
| Lights and Heavies | 0.01173 | 0.773 | 0.0006 | 0.0002 | 0.00025 | 0.014 | 0.06260 | 0.7592 |
| Water | 10.71 | 705.2 | 0.294 | 0.0761 | 1.96 | 105.8 | 49.4 | 599.5 |
| Methanol | 74.6 | 4914.5 | 95.8 | 24.7 | 91.5 | 4939.1 | 0.00 | 0.05 |

The invention claimed is:

1. A process of extracting oxygenates from a hydrocarbon stream, the process including the step of contacting the hydrocarbon stream with an extraction solvent comprising methanol and water in an extraction step, wherein the methanol and water are added separately to the hydrocarbon stream in the extraction step.

2. The process according to claim 1, wherein the hydrocarbon stream is the fractionated hydrocarbon condensation product of a Fischer-Tropsch reaction.

3. The process according to claim 2, wherein the hydrocarbon stream is the fractionated hydrocarbon condensation product of a low temperature Fischer-Tropsch reaction.

4. The process according to claim 3, wherein, prior to extraction, the hydrocarbon condensation product contains 15% to 30% by weight olefins and 5% to 15% by weight oxygenates.

5. The process according to claim 1, wherein the liquid-liquid extraction step takes place in a liquid extraction column and the methanol and water are added separately to the column.

6. The process according to claim 5, wherein the hydrocarbon stream is fed into the extraction column at, or near, the bottom thereof, a methanol stream is fed into the extraction column at, or near, the top thereof, and a water stream is fed into the extraction column between the hydrocarbon stream and methanol stream.

7. The process according to claim 6, wherein a raffinate from the extraction column is sent to a raffinate stripper column from which a hydrocarbon feed stream containing olefins and paraffins and less than 0.2% by weight oxygenates exits as a bottoms product.

8. The process according to claim 7, wherein a raffinate from the extraction column is sent to a raffinate stripper column from which a hydrocarbon feed stream containing olefins and paraffins and less than 0.02% by weight oxygenates exits as a bottoms product.

9. The process according to claim 8, wherein a raffinate from the extraction column is sent to a raffinate stripper column from which a hydrocarbon feed stream containing olefins and paraffins and less than 0.01% by weight oxygenates exits as a bottoms product.

10. The process according to claim 1, wherein an extract from the liquid-liquid extraction step is sent to a solvent recovery column from which a tops product comprising methanol, olefins and paraffins is recycled to the extraction step, thereby enhancing the overall recovery of olefins and paraffins.

11. The process according to claim 10, wherein an aqueous phase of a bottoms product from the solvent recovery column is recycled to the liquid-liquid extraction step.

12. The process according to claim 11, wherein the extraction solvent has a water content of more than 3% by weight.

13. The process according to claim 12, wherein the extraction solvent has a water content of about 5% -15% by weight.

14. The process according to claim 12, wherein the hydrocarbon stream is fractioned in the $C_8$ to $C_{16}$ range.

15. The process according to claim 14, wherein the hydrocarbon stream is fractionated in the $C_{10}$ to $C_{13}$ range.

16. The process according to claim 1, wherein the recovery of olefins and paraffins over the oxygenate extraction process is greater than 70%.

17. The process according to claim 16, wherein the recovery of olefins and paraffins over the oxygenate extraction process is greater than 80%.

18. The process according to claim 1, wherein the olefin/paraffin ratio in the hydrocarbon stream over the oxygenate extraction process is substantially preserved.

* * * * *